United States Patent
Niu et al.

(10) Patent No.: US 8,076,467 B2
(45) Date of Patent: Dec. 13, 2011

(54) NUCLEIC ACID INHIBITORS OF GLUTAMATE RECEPTORS

(75) Inventors: Li Niu, Loudonville, NY (US); Zhen Huang, Albany, NY (US); Hua Shi, Ithaca, NY (US); John T. Lis, Ithaca, NY (US)

(73) Assignees: The Research Foundation of State University of New York, Albany, NY (US); Cornell University, Ithaca, NY (US)

( * ) Notice: Subject to any disclaimer, the term of this patent is extended or adjusted under 35 U.S.C. 154(b) by 66 days.

(21) Appl. No.: 12/578,231

(22) Filed: Oct. 13, 2009

(65) Prior Publication Data

US 2010/0099749 A1 Apr. 22, 2010

Related U.S. Application Data

(62) Division of application No. 11/256,726, filed on Oct. 24, 2005, now Pat. No. 7,601,823.

(60) Provisional application No. 60/621,285, filed on Oct. 22, 2004.

(51) Int. Cl.
| | |
|---|---|
| *C07H 21/02* | (2006.01) |
| *C07H 21/04* | (2006.01) |
| *C40B 40/06* | (2006.01) |
| *C40B 40/00* | (2006.01) |
| *C40B 50/00* | (2006.01) |
| *C40B 30/00* | (2006.01) |
| *A61K 48/00* | (2006.01) |

(52) U.S. Cl. ............. 536/23.1; 506/16; 506/13; 506/23; 506/7; 514/44 R

(58) Field of Classification Search .................. 536/23.1; 506/16, 13, 23, 7; 514/44 R
See application file for complete search history.

(56) References Cited

U.S. PATENT DOCUMENTS 5,270,163 A 12/1993 Gold et al.
7,329,742 B2 2/2008 Doyle et al.

OTHER PUBLICATIONS

Steven M. Shamah et al., "Complex Target SELEX", Accounts of Chemical Research, Jan. 2008, vol. 41(1), 130-138.
Zhen Huang et al., "RNA Aptamers Selected against the GluR2 Glutamate Receptor Channel", Biochemistry 2007, vol. 46, 12648-12655.
Marko Djordjevic, "SELEX experiments: New prospects, applications and data analysis in inferring regulatory pathways", ScienceDirect, Biomolecular Engineering 24 (2007) 179-189.

*Primary Examiner* — Ardin Marschel
*Assistant Examiner* — Lianko Garyu
(74) *Attorney, Agent, or Firm* — Heslin Rothenberg Farley & Mesiti P.C.; Kathy Smith Dias

(57) ABSTRACT

The present invention relates to novel nucleic acid ligands or aptamers that bind to and inhibit the activation of the α-amino-3-hydroxy-5-methyl-4-isoxazole propionate (AMPA) subtype of ionotropic glutamate receptors. Also disclosed is a novel combination of technologies, i.e., SELEX and laser pulse photolysis for the selection and screening of aptamers that inhibit receptor function and are useful therefore, in the treatment of diseases associated with excessive activation of ionotropic glutamate receptors.

13 Claims, 9 Drawing Sheets

| | |
|---|---|
| A1444NB83 | GGGCGAAUUCACUGCCAUCUAGGCAGUAAGCAGGAGUAGUAGGACAAGUUUCGUAACCAGUUAAGAUGGUAAAGUACUACA |
| A1421NB84 | GGGCGAAUUCACUGCCAUCUAGGCAGUUGAGGCUUGAGUUGGAUGCCUGCGCUUAACUGCGAGGUAUACGUAGUACUACA |
| A1229NB84 | GGGCGAAUUCACUGCCAUCUAGGCAGUCUAGGCCUUGUUGGACCAAGAGACACCCACGAAUGGUCGUCACGUCACAAUUGAGUACUACA |
| A1437NB84 | GGGCGAAUUCACUGCCAUCUAGGCAGUCUAGGCCGUCUUCGUGACAAGGUGGAACUUGAUGGUUAGACGAAAAACCCAGAAGUACUACA |
| AN57 | GGGCGAAUUCACUGCCAUCUAGGCAGUAACCAGGAGUAGUAGGACAAGUUUCGUCC |
| A1444NB98 | GGGCGAAUUCACUGCCAUCUAGGCAGUAACCAGGAGUAGUAGGACAAGUUUCGUAACCAGUUAAGAUGGUAAAGUACUA |
| | CAAGCUUCUGGACUCGGU |
| A1444NB86 | GGGCGAAUUCACUGCCAUCUAGGCAGUAACCAGGAGUAGGACAAGUUUCGUAACCAGUUAAGAUGGUAAAGUACUACAAGCU |
| A1421NB87 | GGGCGAAUUCACUGCCAUCUAGGCAGUUGAGGCUUGAGUUGGAUGCGCUGGCCUUAACUGCGAGGUAUACGUAGUACUACAAGCU |
| A1437NB87 | GGGCGAAUUCACUGCCAUCUAGGCCGUCUUCGUGACAAGGUUAGACGAAAAACCCAGAAGUACUACAAGCU |
| A1229NB87 | GGGCGAAUUCACUGCCAUCUAGGCCUUGUUGGACCAAGAGACACCCACGAAUGGUCGUCACGUCACAAUUGAGUACUACAAGCU |

FIGURE 1

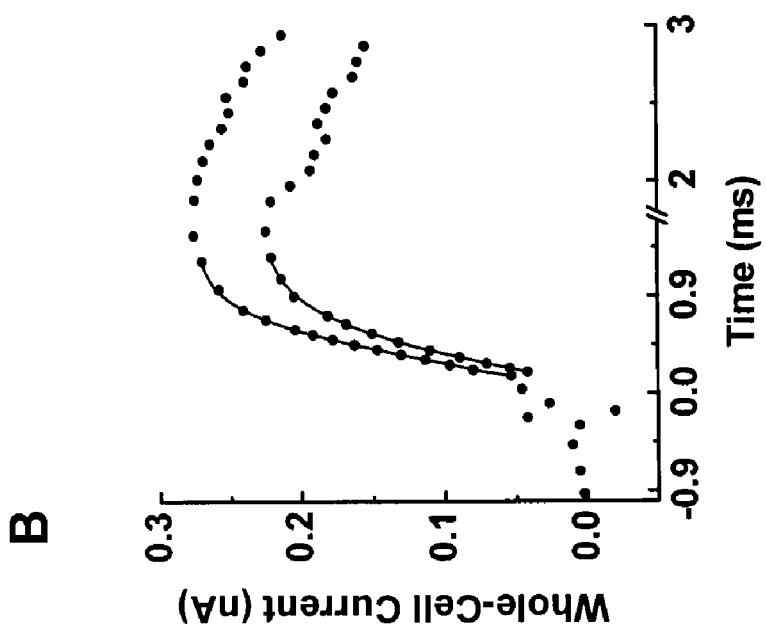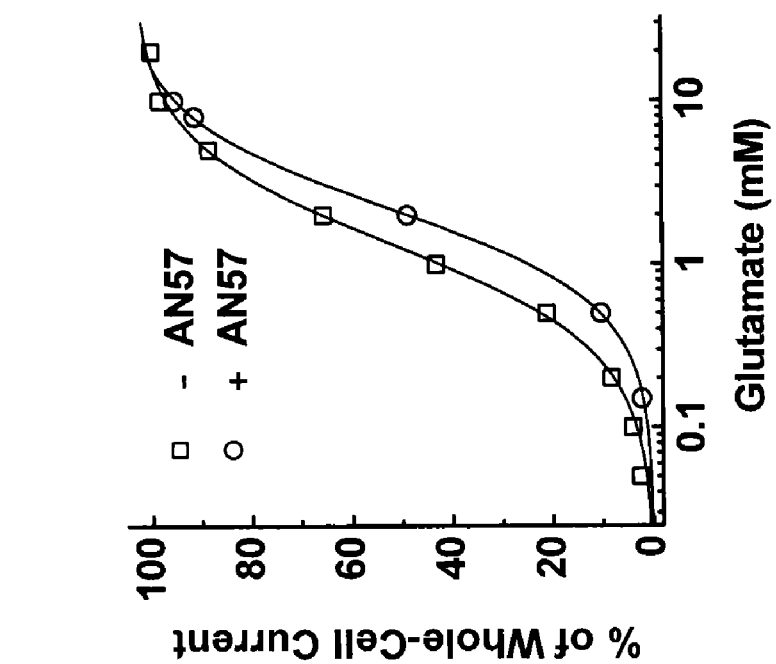
FIGURE 3

NUCLEIC ACID INHIBITORS OF GLUTAMATE RECEPTORS

CROSS-REFERENCE TO RELATED APPLICATION

This application is a divisional of U.S. application Ser. No. 11/256,726 filed on Oct. 24, 2005, which will issue as U.S. Pat. No. 7,601,823 on Oct. 13, 2009; U.S. application Ser. No. 11/256,726 claims priority to U.S. provisional application Ser. No. 60/621,285 filed Oct. 22, 2004, the entire disclosures of each are incorporated herein by reference.

STATEMENT OF RIGHTS UNDER FEDERALLY-SPONSORED RESEARCH

This invention was made with government support under grant W81XWH-04-1-0106 awarded by the U.S. Department of Defense and grant GM60411 awarded by the National Institutes of Health. The government has certain rights in the invention.

FIELD OF THE INVENTION

The invention relates to methods for the identification and preparation of nucleic acid ligands to AMPA glutamate receptors. Included in the invention are specific RNA ligands to AMPA glutamate receptors which inhibit the activity of these receptors.

BACKGROUND OF THE INVENTION

Ion channel glutamate receptors are ligand-gated transmembrane proteins that can be activated by the binding of glutamate, the principal excitatory neurotransmitter in the brain. Ionotropic glutamate receptors (iGluRs) are, therefore, the major excitatory neurotransmitter receptor proteins in the mammalian brain. As such, these receptors play special roles in brain activities, such as memory and learning, and have been implicated in a variety of neurological diseases, such as post-stroke cellular lesion and amyotrophic lateral sclerosis [Dingledine et al., 1999; Heath and Shaw 2002].

When glutamate, released from a presynaptic neuron, binds to a postsynaptic glutamate receptor, the receptor rapidly changes its conformation and transiently forms an open ion channel, thus resulting in a change of the postsynaptic membrane potential. A postsynaptic potential of sufficient strength triggers an action potential, which will in turn propagate the initial nerve impulse. The major function of iGluRs is to mediate fast synaptic neurotransmission underlying the basic activities of the brain, for example, memory and learning. Excessive activation of ionotropic glutamate receptors, particularly the α-amino-3-hydroxy-5-methyl-4-isoxazolepropionate (AMPA) subtype, is known to induce calcium-dependent excitotoxicity. Excitotoxicity has been considered as a general mechanism underlying a number of neurodegenerative disorders such as amyotrophic lateral sclerosis (ALS), stroke, Alzheimer's disease and Parkinson's syndrome.

Using inhibitors to dampen the excessive activity of these receptors may serve as a treatment for neurological disorders such as amyotrophic lateral sclerosis (ALS) or Huntington's disease. To date, Riluzole, an inhibitor of presynaptic glutamate release, is the only drug to produce a significant benefit to the survival of ALS patients. The number of glutamate receptor inhibitors currently available is limited and these inhibitors generally show cross activity to other receptors, for example, kainate receptors. The cross activity is not desirable, because the AMPA and kainate receptors have functional differences. Furthermore, the majority of AMPA receptor inhibitors have poor water solubility. In addition, there is a lack of an assay of inhibitor-receptor interactions within the microsecond (μs) to millisecond (ms) time domain. This is because an AMPA receptor opens its channel in the μs time scale and desensitizes within a few ms in the continued presence of glutamate. Consequently, the affinity of all AMPA receptor inhibitors has been determined only with the desensitized receptors. These deficiencies have significantly hampered drug development.

What is needed, therefore, is an AMPA glutamate receptor inhibitor that is characterized by a high affinity for its target, preferably in the nanomolar range, specificity targeting the glutamate receptor, excellent water solubility and relevance of its inhibitory properties to the functional forms of the receptor rather than the desensitized receptor forms.

SUMMARY OF THE INVENTION

The present invention provides a new class of water-soluble high affinity compounds, specifically nucleic acid ligands or aptamers that inhibit glutamate binding to the AMPA glutamate receptor.

In one aspect, therefore, the invention relates to novel nucleic acid ligands to AMPA receptors. The nucleic acid ligands or aptamers of the invention are selected by an in vitro iterative process of selection, partitioning and amplification referred to as SELEX. Additionally, the nucleotides of the aptamer may be chemically modified either prior to or after selection of the aptamers by SELEX. In one embodiment, the nucleic acid of the invention is an RNA. Examples of glutamate inhibitors of the invention are nucleic acids that have a nucleotide sequence selected from the group consisting of the sequences set forth in SEQ ID NO.: 1 to SEQ ID NO.: 11.

In a related aspect, the present invention relates to a method of identifying a nucleic acid ligand that can inhibit glutamate receptor function, the method comprising the steps of screening a nucleic acid library for a nucleic acid that binds to a glutamate receptor (SELEX); providing a cell that has been transfected to overexpress the glutamate receptor; exposing the cell to glutamate in the presence and absence of the nucleic acid identified by the SELEX method and measuring the glutamate-induced whole-cell current using laser pulse photolysis of caged glutamate as a source of glutamate. The measurements for whole-cell current in the absence and presence of the nucleic acid are compared. A decrease in whole-cell current in the presence of the nucleic acid indicates that the nucleic acid is a specific glutamate receptor inhibitor.

In another aspect, the invention relates to a method of modulating the function of a glutamate receptor comprising contacting a receptor with a nucleic acid ligand that specifically binds the receptor and has been shown to have an inhibitory effect.

In yet another aspect, the invention relates to a pharmaceutical composition comprising the nucleic acids of the invention and optionally, a pharmaceutically acceptable carrier.

In a related aspect, the invention relates to a method of treatment for a disease or condition characterized by excessive activation of ionotropic glutamate receptors, the method comprising administering to the subject in need of such treatment, a therapeutically effective amount of the nucleic acid of the invention.

BRIEF DESCRIPTION OF THE DRAWINGS

FIG. 1 shows the nucleotide sequences (SEQ ID NOs. 1-6 and 8-11) of the nucleic acid ligands of the invention.

FIG. 3(A-B) shows the characterization of the inhibitory properties of one embodiment of the invention, aptamer AN57 with the GluR2Q$_{flip}$ AMPA receptor channel. As shown, AN57 is a competitive inhibitor.

DETAILED DESCRIPTION OF THE INVENTION

Figure 2:
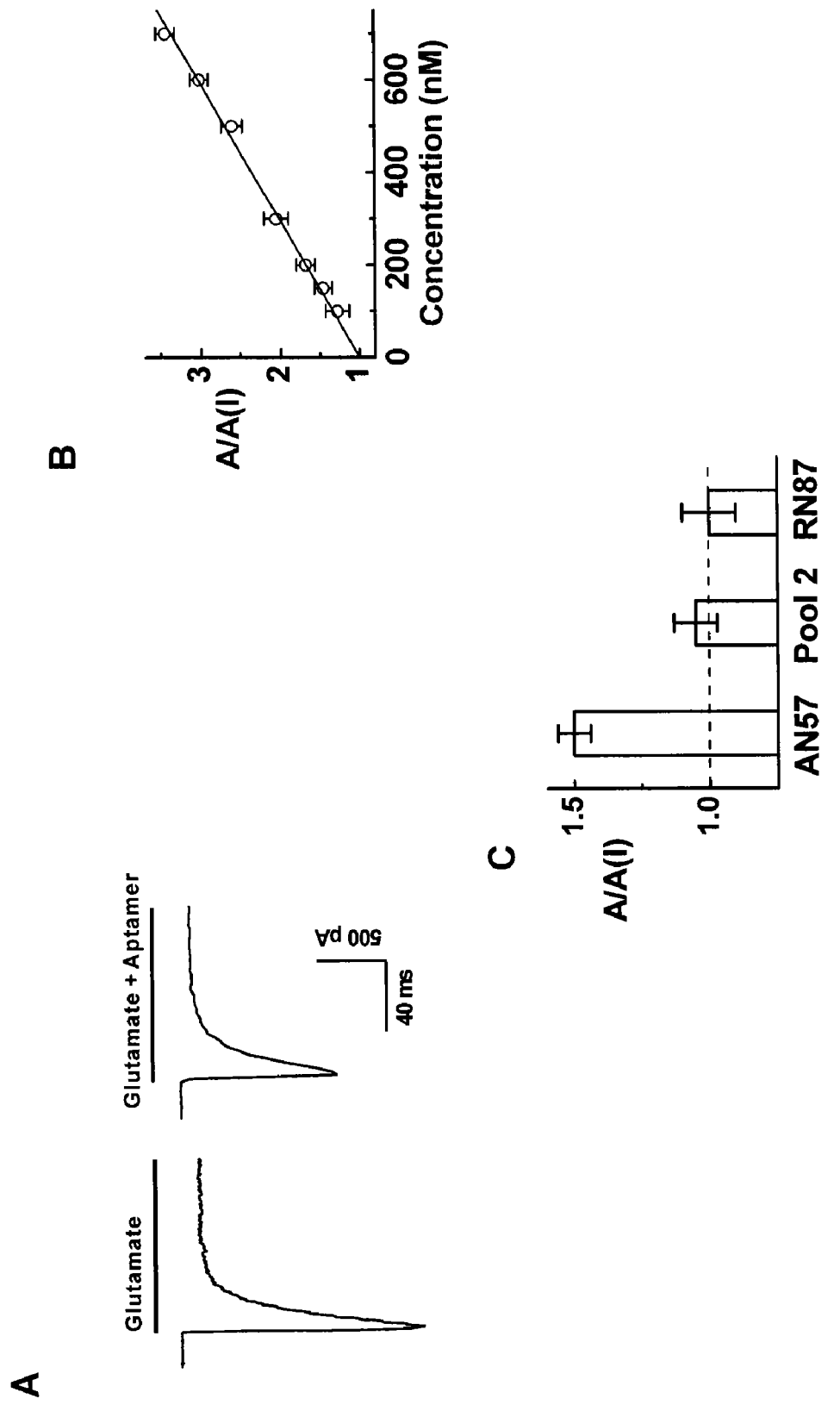
FIG. 2(A-D) shows the results of the determination of the specific inhibition of the GluR2 AMPA receptor by the selected aptamer using whole-cell recording of HEK-293 cell expressing the receptor channel.
Figure 2:
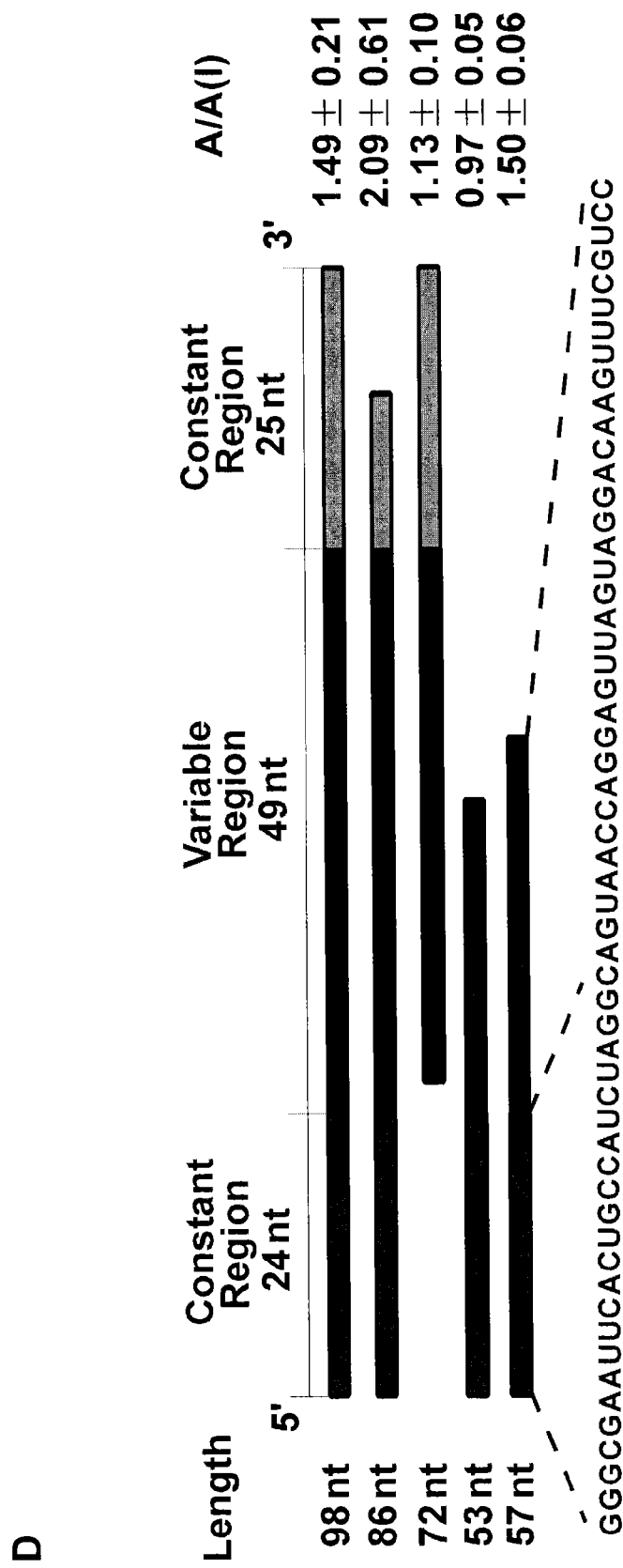

All patents, publications, applications and other references cited herein are hereby incorporated by reference into the present application. In the description that follows, certain conventions will be followed as regards the usage of terminology.

The term "aptamer" refers to a nucleic acid or oligonucleotide molecule that binds to a specific molecular target such as a protein receptor. Aptamers are obtained from an in vitro evolutionary process known as SELEX (Systematic Evolution of Ligands by EXponential Enrichment), which selects target-specific aptamer sequences from large combinatorial libraries of single stranded oligonucleotide templates comprising randomized sequences. Aptamer compositions may be double-stranded or single-stranded, and may include deoxyribonucleotides, ribonucleotides, nucleotide derivatives, or other nucleotide-like molecules. The nucleotide components of an aptamer may include modified or non-natural nucleotides, for example nucleotides that have modified sugar groups (e.g., the 2'-OH group of a ribonucleotide may be replaced by 2'-F or 2'-NH.sub.2). which may improve a desired property, e.g., resistance to nucleases or longer lifetime in blood.

In a preparation of nucleic acids of the invention, individual aptamers having the same nucleotide sequence may differ in their secondary structure. Aptamers may also be conjugated to other molecules, e.g., a high molecular weight carrier to slow clearance of the aptamer from the circulatory system. Aptamers may be specifically cross-linked to their cognate ligands, e.g., by photo-activation of a cross-linker. [Brody, E. N. and L. Gold (2000) J. Biotechnol. 74:5-13.].

The term "nucleic acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

The present invention provides novel nucleic acids that inhibit the activity of ionotropic glutamate receptors, and in particular, the α-amino-3-hydroxy-5-methyl-4-isoxazole-propionate (AMPA) subtype of glutamate receptors. The nucleotide sequence of examples of nucleic acids of the invention are shown in FIG. 1.

The present invention further provides a novel method of identifying nucleic acids which specifically bind to and inhibit the function of glutamate receptors such as the AMPA receptor. The method comprises first screening a nucleic acid library for a nucleic acid that binds to a glutamate receptor. A modified SELEX method was used to identify the nucleic acid ligands disclosed herein. Once a glutamate receptor-specific aptamer has been identified, the aptamer's ability to inhibit glutamate function is evaluated. By providing a cell that has been transfected to overexpress the glutamate receptor and measuring glutamate-induced whole-cell current in a single cell in the presence and absence of the nucleic acid identified by SELEX, a comparison of the measurement of whole cell current in the presence and absence of nucleic acid is informative of the aptamer's potential as a glutamate receptor inhibitor. A decrease in the whole-cell current in the cell in the presence of nucleic acid as compared to the whole-cell current in the absence of nucleic acid indicates that the nucleic acid inhibits glutamate receptor function.

To arrive at the novel inhibitors of the present invention, therefore, a novel combination of two approaches was used, namely an in vitro iterative procedure, SELEX, to select the aptamers of the invention from a combinatorial RNA library and a laser-pulse photolysis technique that has a microsecond (μs) time resolution to screen the aptamers against a functional (i.e., non-desensitized) form of the glutamate receptor.

Aptamers that recognize the AMPA receptors may be selected in a number of ways. In one embodiment, aptamers are selected from a combinatorial library using SELEX, by immobilizing intact cells containing the glutamate receptor on a biosensor chip and monitoring using a surface plasmon resonance (SPR) technique. SPR is an optical technique that offers real time analysis of the rates of adsorption and desorption for a range of surface interactions. In an alternate embodiment, a cell membrane preparation, for example from a cell that has been transfected to overexpress the target receptor, may be used as the selection target.

Known inhibitors for the receptor, for example, NBQX, philanthotoxin-343 and GYM 47261 are used to displace all specific RNAs previously bound to the receptor. The consensus sequences in the aptamers are then identified by cloning and sequencing to identify inhibitor candidates.

Prior to screening the aptamers for inhibitory activity, the target receptor subunits are expressed at an enhanced efficiency by transfecting cells, for example, HEK-293 cells with a nucleic acid encoding the receptor subunit(s) in conjunction with a nucleic acid encoding simian virus (SV) 40 T antigen. Methods for the construction of an appropriate vector and for transfection of an appropriate host cell are well known to those of skill in the art and are described, for example, in Sambrook et al., 2001, *Molecular Cloning: A Laboratory Manual*, Third Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984 (M. L. Gait ed.)

To elucidate the channel opening kinetics of the homomeric channel with and without aptamer ligand, a rapid kinetic technique that has a microsecond time resolution, namely laser pulse photolysis of caged glutamate, is used. The channel opening rate constant, the channel closing rate constant or the lifetime of the channel, and the dissociation equilibrium constant for glutamate are determined. Thus, by this methodology, the mechanism of action, the affinity, and selectivity of each aptamer on the functional forms of each receptor subunit can be characterized.

Each of the steps of the method for identifying nucleic acid ligands that may useful as glutamate receptor inhibitors are discussed in detail below.

Aptamer Selection by SELEX

A method for the in vitro evolution of nucleic acid molecules with high affinity binding to target molecules is known to those of skill in the art and is described in U.S. Pat. No. 5,270,163. The method, known as SELEX (Selective Evolution of Ligands by EXponential Enrichment) involves selection from a mixture of candidate oligonucleotides from a library comprising a large sequence variations (in the present case, ~$10^{15}$) and step-wise iterations of binding, partitioning and amplification, using the same general selection theme, to achieve virtually any desired criterion of binding affinity and selectivity.

Starting from a mixture of nucleic acids, preferably comprising a segment of randomized sequence, the SELEX method includes the steps of contacting the mixture with the desired target, partitioning unbound nucleic acids from those nucleic acids which have bound to the target molecule, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield high affinity nucleic acid ligands to the target molecule.

The SELEX method may be modified to encompass the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described, for example, in U.S. Pat. No. 5,660,985. These include oligonucleotides containing nucleotide derivatives chemically modified at the 2' position of ribose, 5 position of pyrimidines, and 8 position of purines. U.S. Pat. No. 5,756,703 describes oligonucleotides containing various 2'-modified pyrimidines. U.S. Pat. No. 5,580,737 describes highly specific nucleic acid ligands containing one or more nucleotides modified with 2'-amino (2'-NH.sub.2), 2'-fluoro (2'-F), and/or 2'-O-methyl (2'-OMe) substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand.

In one embodiment, the selection of a nucleic acid ligand specific for the target of interest may be carried out on a sensor chip surface and monitored by SPR. A combinatorial RNA library is made by transcribing DNA templates or a DNA library. Each template consists of 108 bases with a 40-base randomized segment. This segment is flanked by two constant regions for primer annealing. The 5' constant sequence includes a promoter for T7 RNA polymerase. The two restriction sites are EcoRI located in the 5' constant region and HindIII located in the 3' constant region, respectively.

Rat motor neurons contain all AMPA receptor subunits and may be used as the protein target in SELEX. The motor neurons are dissected from the spinal cord of 15-day old embryonic rats, and purified by "panning" the cells in a Petri dish pre-coated with an anti-mouse IgG, 192-IgG, which recognizes the p75 neurotrophic factors that are solely expressed in the 15-day-old motor neurons.

The binding of RNAs to AMPA receptors (step 1) is carried out on a biosensor chip surface and monitored using the SPR technique in real time. In one embodiment, 192-IgG is covalently immobilized on a CMS sensor chip using a standard carbodiimide reagent. Then the motor neurons are tethered onto the sensor chip surface by binding to the antibody. The RNA molecules are injected into the reaction cell. Those that can bind to the AMPA receptors on the motor neurons immobilized on the surface will be retained. The RNA selection reaction is carried out at 22° C. in the presence of anti-RNAse. One of the advantages of this sensor technique is that as low as pictogram quantity of the protein is sufficient for selection. The binding of RNAs register as a net increase of SPR signal, while the subsequent elution of the bound RNAs in the presence of known inhibitors results in a fall of the SPR signal. Both processes are monitored in real time.

A mixture of known inhibitors is injected into the reaction cell (step 2). The RNA molecules bound to the motor neurons at the same and/or mutually exclusive sites will be eluted all at once, and collected. For purposes of practicing the present invention, inhibitors include, NBQX (a competitive inhibitor), philanthotoxin-343, a wasp neurotoxin analog (non-competitive inhibitor) and GYKI 47261, a 2,3-benzodiazepine derivative. The collected RNAs are reverse-transcribed and amplified by PCR (step 3). The new RNA pool is prepared by transcription. A new round of selection can then proceed from step 1. The SELEX progress is monitored for the level of SPR signal generated by the binding of the RNAs from a certain round, for instance, the selection is completed when the maximum SPR signal between two consecutive rounds no longer changes. When SELEX is completed (usually 8-12 rounds), the cDNA pool is cut with EcoRI and HindIII at the constant regions and ligated into the vector pGEM-3Z. Colonies are sequenced and the consensus sequences identified.

In a preferred embodiment, using an improvement to SELEX technology, aptamers against a membrane-bound receptor were identified using, as the target, cell membranes from fragmented HEK-293 cells that had been transfected to overexpress the receptor. The RNA library was described previously (Fan, X., Shi, H., Adelman, K. & L is, J. T. Probing TBP interactions in transcription initiation and reinitiation with RNA aptamers that act in distinct modes. *Proc Natl Acad Sci U S A* 101, 6934-9). The in vitro transcribed RNA was dissolved in extracellular buffer (see buffer composition below) at a final concentration of 20 μM. The RNA library was heated at 70° C. for 10 min before use. The fragmented HEK-293 cell membrane was prepared in accordance with methods known to those of skill, and the membrane-bound receptor was adjusted to a final concentration of 50 nM, as determined by [$^3$H]AMPA binding. The reaction mixture was incubated at 22° C. for 40 min for RNA binding in the presence of 0.3 units/μl RNase inhibitor (Ambion, Austin, Tex.). In an improvement of the SELEX technology, reaction mixture containing the nucleic acid-target complexes was passed through a nitrocellulose filter using a filtration apparatus (Pierce, Rockford, Ill.) to wash off unbound RNAs. The desired RNAs were eluted using 1 mM-NBQX and were then subjected to reverse transcription and PCR. A new RNA pool was then transcribed, and a new round of selection was repeated. Overall, 15 rounds of SELEX were performed, including 3 negative selections using HEK-293 cell membrane that did not express any AMPA receptor. About 120 clones from rounds 12, 14 and 15, were sequenced. The clones harboring consensus sequences were identified and assayed for inhibition.

In order to establish a baseline for the characterization of the efficacy and selectivity of each aptamer, the channel opening kinetics of each of the AMPA receptor subunits was determined using the measurement of glutamate-induced whole cell current in AMPA receptor-bearing cells. To improve the current response of a single cell, however, it is desirable to enhance the expression of the receptor of which the activity is to be measured. A method for enhancing protein expression in single HEK 293 is summarized below (Huang et al., Journal of Neruoscience Methods, 142:159-166 2005.)

Transfection or Enhanced Expression of GluR2Q$_{flip}$

Recombinant proteins are routinely expressed in heterologous expression systems, such as human embryonic kidney 293 (HEK 293) cells. The efficiency of the expression is critical when the expressed protein must be characterized at the single-cell level. A simple method by which the protein expression efficiency in single HEK 293 cells is enhanced by coexpressing simian virus 40 large T antigen (TAg), a powerful oncoprotein. Using this technique, GluR2 ionotropic glutamate receptor expression in single HEK 293S cells increased approximately seven-fold. The ratio of the plasmid amount of TAg to that of the receptor was optimized at 1:10, while the receptor function was unaffected in the presence of TAg. Fluorescence imaging of a population of cells was used as an independent detection method and a similar increase in expression of green fluorescent protein (GFP) by TAg coexpression was found. Thus, this method is suitable for enhancing the expression of both membrane and soluble proteins at the single-cell level for purposes of practicing the present invention. Additionally, the function of a protein can be studied directly in intact cells, a feature particularly useful for studying membrane proteins.

Enhance expression efficiency is achieved by coexpression of simian virus (SV) 40 large T antigen (TAg), a powerful oncoprotein (Ali and DeCaprio, 2001; Chen and Hahn, 2003; Simmons, 2000; Sullivan and Pipas, 2002), with the protein of interest. Specifically, a nucleic acid encoding the protein of interest is harbored in a plasmid containing the SV40 replication origin, and the TAg gene is encoded in a separate vector. Transient coexpression of TAg produces more proteins of interest per cell. Specifically, TAg enhancement of the single-cell expression of GluR2, a key glutamate receptor subunit (Li et al., 2003b), was characterized to establish the optimal plasmid ratio and the most complementing cell line. The function of the GluR2 receptor within intact cells was further characterized without removing TAg. In addition, using green fluorescence protein (GFP) (Chalfie et al., 1994) as a reporter gene and fluorescence imaging of a population of HEK 293 cells as an independent detection method, it was shown that GFP expression in these cells increased similarly.

Therefore, a plasmid encoding each of the AMPA receptor subunits, GluR1-4, and the GluR6Q kainate receptor subunit was used to transiently express the corresponding homomeric channel in HEK-293S cells by a standard calcium phosphate method. As a cell marker for electrophysiological recording but not for SELEX, the cell was cotransfected with the plasmid encoding green fluorescent protein (GFP). The ratio by weight of the plasmid of GFP to that of a receptor was 1:10 and the receptor plasmid used was ~3-10 μg/35 mm Petri dish. The SV40 large T-antigen (TAg) gene was also cotransfected to enhance the single-cell receptor expression, as we previously reported. The ratio of the plasmid by weight for TAg to that of a receptor was 1:10. The cells were maintained in Dulbecco's modified Eagle's medium supplemented with 10% fetal bovine serum (all from Invitrogen, Carlsbad, Calif.), in a 37° C., 10% $CO_2$, humidified incubator. 48 hours after transfection, the cells were either used for patch clamping or harvested for SELEX.

Exploiting the enhanced expression of the AMPA glutamate receptor in transfected cells, the ability of the nucleic acid aptamers of the invention to impact glutamate receptor function was evaluated.

Whole-Cell Current Measurement

Glutamate, a natural neurotransmitter, was used as the activating ligand, and the resulting receptor response in a single cell was recorded. Recording electrodes were made from glass capillary pipettes and fire polished. The electrode resistance was ~3 MΩ when filled with the electrode solution. The electrode solution contained 110 mM CsF, 30 mM CsCl, 4 mM MaCl, 0.5 mM $CaCl_2$, 5 mM EGTA, and 10 mM Hepes (pH 7.4 adjusted by CsOH). The external bath solution contained 150 mM NaCl, 3 mM KCl, 1 mM $CaCl_{2,1}$ mM $MgCl_2$ and 10 mM Hepes (pH7.4 adjusted by NaOH). The GFP fluorescence in transfected cells was visualized using an Axiovert S100 microscope with a fluorescent detection system from Carl Zeiss (Thornwood, N.Y.). The whole-cell current was recorded using an Axonpatch-200B amplifier at a cutoff frequency of 2-20 kHz by a built-in eight-pole Bessel filter and digitized at 5-50 kHz sampling frequency using a Digidata 1322A from Axon Instruments (Union City, Calif.). The data acquisition software was pCLAMP 8, also from Axon Instruments.

Laser-Pulse Photolysis

Laser pulse photolysis using caged neurotransmitters has been designed to measure the receptor channel opening kinetics and inhibitor-receptor interaction with a μs time resolution. Caged neurotransmitters are biologically inert, but photolabile precursors of neurotransmitters. This technique utilizes a rapid photolytic release of a neurotransmitter from the caged precursor within the μs time domain to overcome the otherwise slow diffusion and mixing of free neurotransmitters with the receptor on the surface of a cell. Using this technique, the opening of a receptor channel can be measured prior to receptor desensitization. To study glutamate receptors, caged glutamate was developed and is commercially available. The setup for the laser-pulse photolysis experiment is described elsewhere [Matsubara et al., *Biochemistry* 31:5507-14, 1992; Niu et al., *Chemical kinetic investigations of neurotransmitter receptors on a cell surface in a microsecond time region*, Vol. VII, Academic Press, New York, 1996]

For purposes of practicing the method of the present invention, αCNB glutamate (caged glutamate) from Molecular Probes (Eugene, Oreg.) was dissolved in the external bath buffer and delivered over the surface of a HEK-293 cell expressing a receptor using a U-tube made from stainless steel tubing with a hole of ~150 μm in diameter. The addition of the solution containing the ligand and the suction of the waste are controlled by two peristaltic pumps. A HEK-293 cell is ~15 μm in diameter. The cell suspended from the current-recording electrode is ~100 μm away from the hole. The linear flow rate of the solution is 1-4 cm/s. An optical fiber through which laser light for photolysis is delivered to the cell has a core diameter of 300 μm. The relative distance between the cell and the fiber is ~400 μm.

A U-tube flow device was used to apply glutamate or the caged glutamate (Molecular Probes, Eugene, Oreg.) in the absence and presence of aptamer to a cell expressing the receptor of interest. The current traces were sampled at 5-50 kHz and filtered at 2-20 kHz by an 8-pole Bessel filter. The data were acquired using pCLAMP 8 (Axon Instruments, Union City, Calif.). In the laser-pulse photolysis measurement of the channel-opening process of the GluR2 AMPA receptor, the caged glutamate dissolved in the external bath buffer was photolyzed to release free glutamate in the microsecond time region to activate the receptor channel. A laser pulse from the third harmonic output (355 nm, 8 ns pulse length) of a Minilite II pulsed Q-switched Nd:YAG laser (Continuum, Santa Clara, Calif.) was used in the photolysis measurement. All whole-cell recordings were at −60 mV and 22° C.

Once a HEK-293 cell is in the whole-cell mode, it is lifted from the bottom of the dish and suspended in the external bath solution. After the cell is equilibrated with caged glutamate for 250 ms, a laser pulse at 355 nm with a pulse length of 8 ns is generated from a Minilite II pulsed Q-switched Nd:YAG laser from Continuum (Santa Clara, Calif.) tuned by a third harmonic generator. The laser light was coupled into a fiber optic from FiberGuide Industries (Stirling, N.J.) and the power was adjusted to be 200-800 μJ, detected by a Joulemeter from Gentec (Quebec, Canada).

The concentration of the photolytically generated glutamate is determined by the following method. Known concentrations of free glutamate are applied to a HEK-293 cell, using the flow device. The current amplitude obtained is corrected for desensitization using a standard protocol and compared with that obtained from the laser-pulse photolysis experiment (this is also a means of assaying whether repetitive laser pulses have damaged the cell).

In general, a receptor-mediated reaction can be written as follows:

$$A + L \underset{}{\overset{K_1}{\rightleftharpoons}} AL_n \underset{}{\overset{\Phi}{\rightleftharpoons}} \overline{AL_n} \text{ (open)} \quad (1)$$

$$I_t = I_{max}[1-\exp(-k_{obs}t)] \quad (2)$$

$$k_{obs} = k_{cl} + k_{op}\left(\frac{L}{L+K_1}\right)^n$$

A represents the active form of the receptor, L, the ligand concentration, $AL_n$, the closed-channel forms of the receptor, and $\overline{AL_n}$ the open-channel form, $K_1$ the intrinsic dissociation constant of activating ligand and D the channel opening equilibrium constant ($\Phi=k_{cl}/k_{op}$). The $k_{cl}$ is the channel closing rate constant or the lifetime of the channel, $k_{op}$ is the channel opening rate constant, and n is the number of ligand binding sites.

Based on this mechanism, the current rises exponentially (Equation 1) due to channel opening. In Equation 1, $I_t$ represents the current observed at time t, and $I_{max}$ is the maximal observed current in the absence of receptor desensitization (assuming that the desensitization occurs after the channel opening). The relationship between the observed first-order rate constant for the channel opening and constants for the general mechanism is shown in Equation 2. The derivation of this equation assumes that binding of ligand is fast compared to the channel opening process. Plotting the $k_{obs}$ value vs. the concentration, L, of the photolytically released glutamate will yield the constants, $k_{cl}$, $k_{op}$, $K_1$, and n using Equation 2.

Whenever possible, independent approaches are applied to verify some of the results obtained from the laser pulse photolysis experiments. For instance, $k_{cl}$, the channel closing rate constant, is the same as lifetime of the channel obtained from signal channel recording technique. In laser pulse photolysis experiments, a concentration of the photolytically released ligand as high as 400 μM has been obtained without damaging the cell. Obtaining a higher concentration is neither practical nor necessary. A higher concentration release requires a higher laser power, which will damage or even destroy the cell. Furthermore, a ligand concentration at 400 μM or even less is generally sufficient to apply the described method to the determination of the receptor channel opening kinetics.

The mechanism of inhibition of each AMPA receptor channel by the selected aptamers is investigated and the affinity of an aptamer for both the closed and open forms is measured. The selectivity of an aptamer for all the four AMPA receptor subunits is also determined.

The mechanism of inhibition can be determined by studying the effect of an inhibitor on the channel opening rate process. For instance, an inhibitor can bind only to the closed channel forms (Mechanism 1: open channel blockade) or it binds to both the closed and open channel forms (Mechanism 2: noncompetitive mechanism). The observed rate constant, $k_{obs}$, in the presence and absence of inhibitor can be measured using Equation 1 (in Aim II). The relationship of the $k_{obs}$ to the molar concentration of the ligand (glutamate), L, and the inhibitor, I, can be written according to the individual mechanism; for example, for open channel blockade (mechanism 1), Equation 3 can be used:

$$k_{obs} = k_{op}\left(\frac{L}{L+K_1}\right)^n + k_{cl}\left(\frac{\overline{K_I}}{\overline{K_I}+I}\right) \quad (3)$$

For the noncompetitive mechanism (2), the following equation (4) would be used:

$$k_{obs} = k_{op}\left(\frac{L}{L+K_1}\right)^n\left(\frac{\overline{K_I}}{\overline{K_I}+I}\right) + k_{cl}\left(\frac{\overline{K_I}}{\overline{K_I}+I}\right) \quad (4)$$

In deriving these equations, one binding site for inhibit per receptor molecule is assumed for simplicity. At low concentrations of glutamate (L<<$K_1$), $k_{obs}$ reflects the channel closing rate constant since the contribution of the $k_{op}$ portion in Equations 2, 3 and 4 to the overall rate, $k_{obs}$, is minimal. Under this condition, the effect of the inhibitor on the $k_a$ can be measured. In this case, for both Mechanisms 1 and 2, the effect of the inhibitor on the $k_a$ are the same and can be obtained by Equation 5, which can be derived from either Equation 3 or 4. From Equation 5, the dissociation constant of the inhibitor from the open channel form, $K_1$, can be uniquely determined.

The effect of the inhibitor on $k_{op}$ is obtained at high ligand (glutamate) concentrations (where $k_{obs}$ is $>>k_{cl}$). For Mechanism 1, the inhibitor does not affect $k_{op}$ (Equation 6). For Mechanism 2, the inhibitor affects both $k_{cl}$ and $k_{op}$ (Equation 7). Thus, based upon the effects of an inhibitor on both $k_{cl}$ and $k_{op}$, the mechanism of action of an inhibitor can be differentiated. Furthermore, the dissociation constant of the inhibitor for the closed channel form $K_I$ can be uniquely determined for Mechanism 2, the noncompetitive inhibition. In summary, a complete understanding of the mechanism of action of a inhibitor cannot be achieved without the knowledge of the effects of the inhibitor on both $k_{cl}$ and $k_{op}$. Experimentally, the time resolution provided by the laser pulse photolysis technique makes it possible to measure these effects.

$$k_{obs} = k_{cl}\left(\frac{\overline{K_I}}{K_I + I}\right) \quad (5)$$

$$k_{obs} - k_{cl}\left(\frac{\overline{K_I}}{K_I + I}\right) = k_{op}\left(\frac{L}{L + K_I}\right) \quad (6)$$

$$k_{obs} - k_{cl}\left(\frac{\overline{K_I}}{K_I + I}\right) = k_{op}\left(\frac{L}{L + K_I}\right)^n\left(\frac{\overline{K_I}}{K_I + I}\right) \quad (7)$$

For clarity of the discussion, only two mechanisms are described above to illustrate the principle of how different mechanistic models can be differentiated. In practice, different models such as competitive mechanism can be formulated and tested similarly. The method of model differentiation described concerns only the measurement of rate constants. In fact, the ratio of the current amplitude in the presence and absence of an inhibitor is not only informative but also diagnostic. The amplitude ratio can be used to independently obtain affinity constants for inhibitors and to verify them with those obtained from rate constant measurements. Experimentally, the rate constant and the maximum current amplitude are collected from a single laser pulse photolysis experiment and both are used. The methodology for determining the mechanism and efficacy of an inhibitor is based upon the measurement of the current from a sum of receptors (either in a whole cell or in a patch), rather than from a unitary conductance level as observed in single channel recording. Therefore, the method described is particularly useful to deal with a low conductance signal, which has so far limited the study of the GluR2 channel by single channel recording.

The present invention relates to the discovery and characterization of a group of water-soluble AMPA receptor inhibitors, which are RNA aptamers that can fold into unique three-dimensional structures that confer high affinity and specificity against biological targets. Using patch-clamp recording as a functional assay, we found that these aptamers reproducibly inhibited the glutamate-induced whole-cell current from the human embryonic kidney (HEK)-293 cells expressing the GluR2Q$_{flip}$ receptor. The determination of the specific inhibition of the GluR2 AMPA receptor by the selected aptamer using whole-cell recording of HEK-293 cells expressing the receptor channel is shown in FIG. 2. FIG. 2A depicts the whole-cell current response to 500 μM glutamate in the absence and presence of 75 nM AN57. Inhibition by AN57 was concentration-dependent, as shown in FIG. 2B, with the $K_{I,app}$ for AN57 determined to be 296±10 nM from the plot of the whole-cell current in the absence, A and presence, A(I), of AN57 using Equation 1, yielding the intrinsic inhibition constant ($K_I$) of 133±5 nM calculated using Equ. 8. The specific inhibition of the GluR2 channel by aptamer AN57 was verified by using pool 2, the second-round library, or RN87, a different sequence from AN57. Neither the library of randomized sequences nor different sequence showed any inhibition (FIG. 2C).

Next, we determined the minimized, yet fully functional, sequence. Guided by the secondary structure prediction using the Mfold program and by the activity assay using whole-cell recording, the sequence of the original 98-nt aptamer was truncated from both ends (FIG. 2D) and the corresponding versions were tested using whole-cell recording. Removal of 26 nucleotides (nt) from the 5' direction (a constant region of the sequence template) resulted in a total loss of inhibitory function, suggesting that this sequence plays an essential role, likely a structural one, for the aptamer function. In contrast, progressive reduction of the sequence from the 3' end showed that a 57 nt version retained the activity whereas the 53 nt version did not (FIG. 2D). The deletion of 4 more nucleotides at the 3' end of the 57-nt version presumably disrupted critical base paring, as predicted by Mfold. Thus, the 57-nt aptamer became the minimized working template for the subsequent structural and functional studies.

Figure 6:
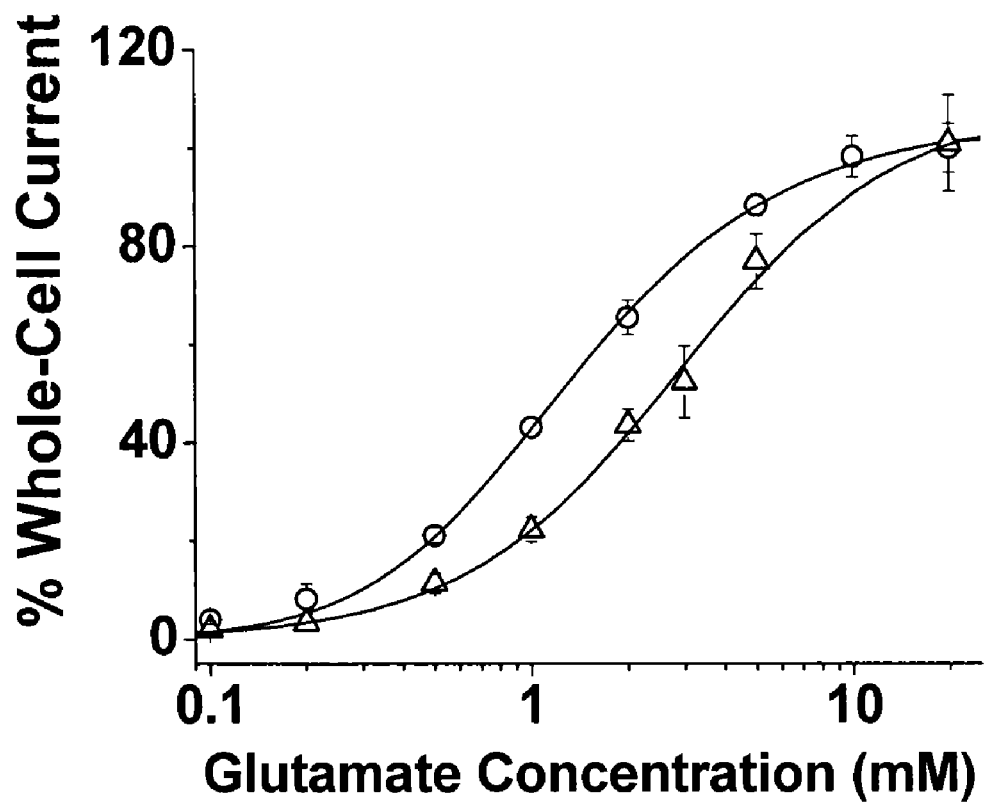
FIG. 6 is a graph that shows the dependence of the whole-cell current response of the GluR2Q$_{flip}$ receptor channel to glutamate in the absence (upper curve) and presence (lower curve) of 5 mM NBQX. This shows NBQX is a competitive inhibitor.

In this successful selection of the aptamer, the GluR2 AMPA receptor subunit was chosen to be the selection target because of its key role in mediating the calcium-dependent neuronal toxicity. Experimentally, GluR2 was expressed in HEK-293 cells and the membrane that harbored the functional channel was used for SELEX. Thus, the aptamers selected would be expected to recognize the total, functional GluR2 receptor. Furthermore, NBQX was chosen to selectively "elute" the aptamers that were bound to the NBQX site or to a mutually exclusive site(s) on the receptor. The choice of NBQX was based on both its medical relevance and its known mechanism of action as a competitive inhibitor. Consequently, the selected aptamers would be predicted to be competitive inhibitors as well. To confirm this, the dose response relationship of glutamate with the GluR2Q$_{flip}$ channel was measured in the absence and presence of aptamer. As shown in FIG. 3A, the two curves converged at saturating concentrations of agonist, which is characteristic of competitive inhibition, indicating that AN57 competitively inhibited the GluR2 AMPA receptor. The effect of the aptamer on the dose-response curve is actually similar to the effect of NBQX, a known inhibitor (FIG. 6). Using a laser-pulse photolysis technique with caged glutamate, the rate of the receptor channel opening was measured (FIG. 3B). The observed rate constant of the GluR2Q$_{flip}$ channel opening was slowed, as expected, in the presence of aptamer. It should be further noted that the laser-pulse photolysis technique offered a ~60 μs time resolution. Such time resolution was sufficient to enable us to measure the rate of channel opening before the receptor desensitization—a reaction that leads to a glutamate-bound, but channel-closed, thus inactive, receptor state. This technique therefore permits a critical screening of aptamers.

The nanomolar affinity of aptamer AN57 (i.e., $K_I$=133 nM) compares favorably with the micromolar affinity values generally found for AMPA receptor inhibitors prepared synthetically. However, as compared with NBQX, the "elution pressure" used in our SELEX, the affinity of the aptamer is >10- fold lower. At least two possibilities might explain the lower affinity of the aptamer. First, the sequence identified from the RNA library may not confer the most optimized secondary structure, and we are attempting to select derivatives with higher affinity by library doping based on the existing sequence. Second, there might be multiple aptamer structures folded from the same sequence during the in vitro transcription, and yet only one might be functional. If so, the $K_I$ of 133 nM would be an over-estimated value for the functional structure in the mixture of all structures.

Figure 4:
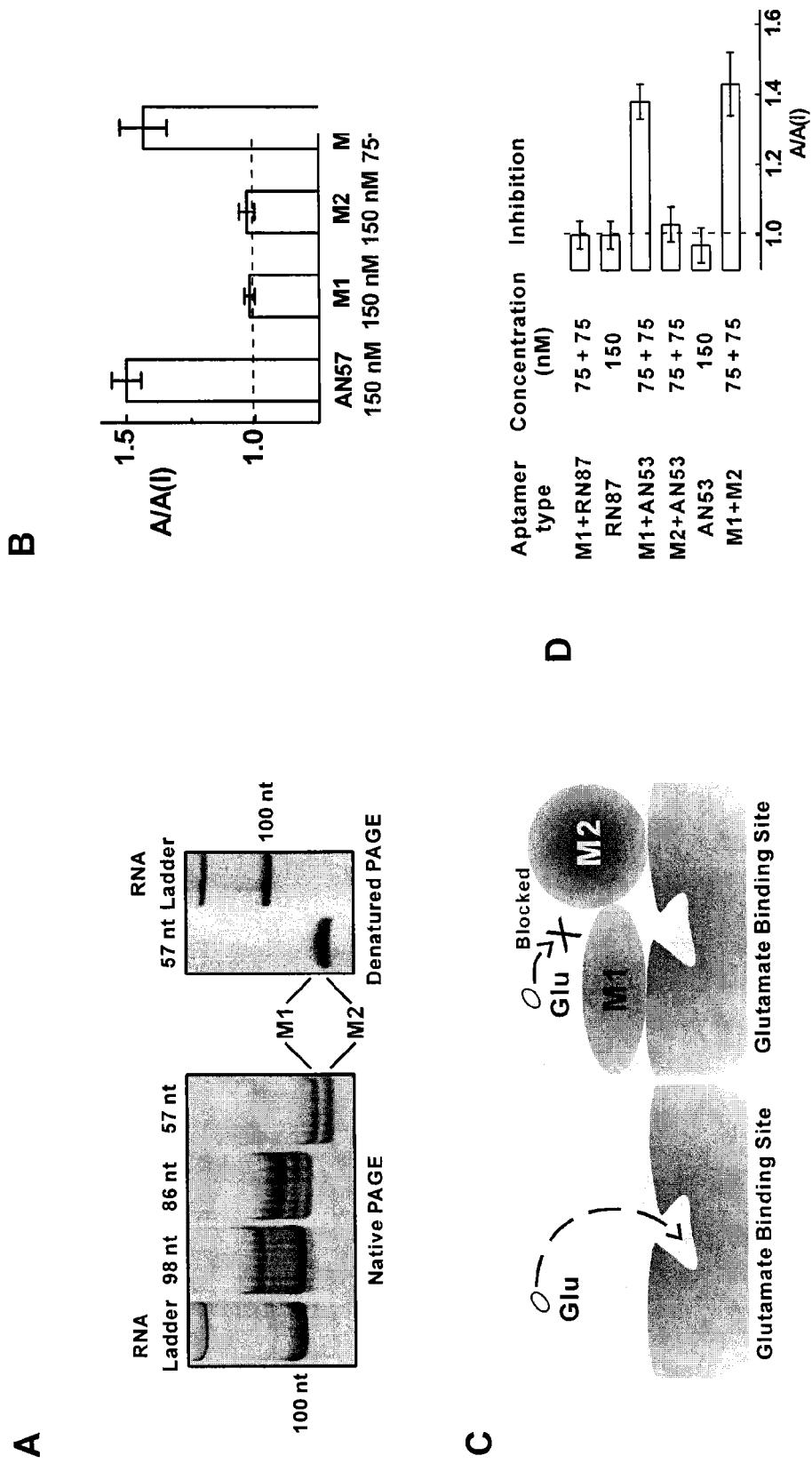
FIG. 4(A-D) shows a proposed mechanism of action of aptamer AN57, which, in one embodiment assumes two structurally distinct species, both of which are required for inhibition.

To investigate this possibility, we examined the in vitro RNA transcripts on a native polyacrylamide gel (PAGE) (FIG. 4A). Two major bands were observed, and termed as M1 and M2 (FIG. 4A, left panel). The difference in mobility in the native gel between M1 and M2 is indicative of different structural features assumed from the same sequence, as only a single sharp band was seen in denaturing gel (FIG. 4A, right panel). Furthermore, these two major structures were visible throughout the sequence reduction but were the clearest in the 57-nt aptamer (FIG. 4A).

Surprisingly, the functional test showed that neither M1 nor M2 alone was inhibitory (FIG. 4B); but when combined, the inhibitory activity was fully restored, as compared to the original, in vitro transcribed sample (FIG. 4B). Based on these results, we propose a simple model by which (FIG. 4C) binding of both M1 and M2 to their sites is sufficient to sterically block the entry of glutamate. Binding of either M1 or M2 alone, however, is insufficient to set up the steric barrier to block the entrance of the glutamate binding site. Note that this model (FIG. 4C) is also consistent with the competitive nature of the inhibition by the aptamer (FIG. 3A).

Figure 7:
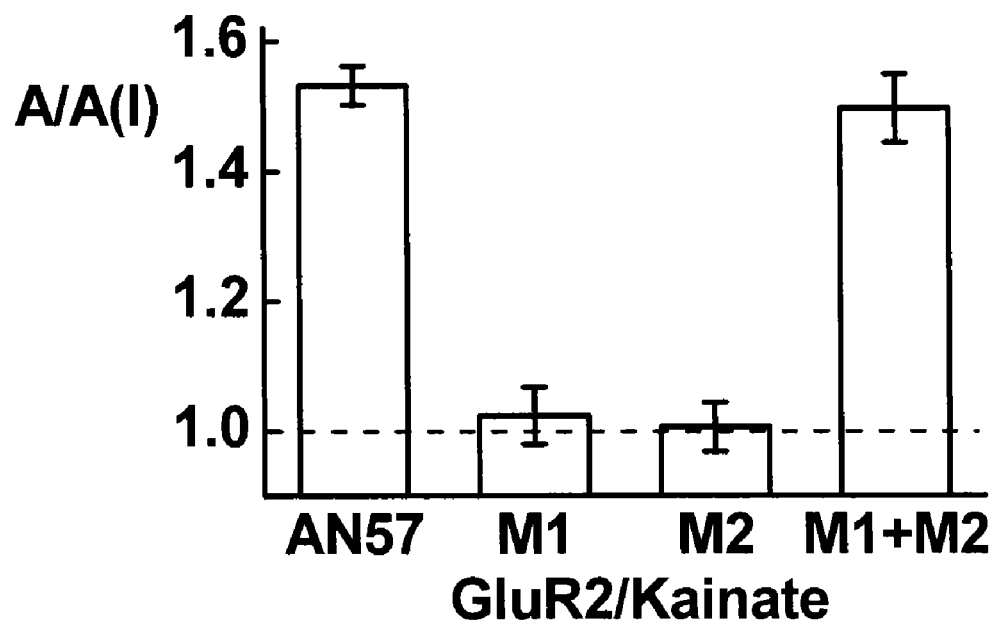
FIG. 7 shows that when purified, aptamer AN57 assumes two structures (M1 and M2) either of which individually does not inhibit the whole-cell response to kainate (kainate was used to induce the GluR2Q$_{flip}$ AMPA receptor response). Inhibition seen with unpurified AN57 is restored when the M1 and M2 are recombined.
Figure 8:
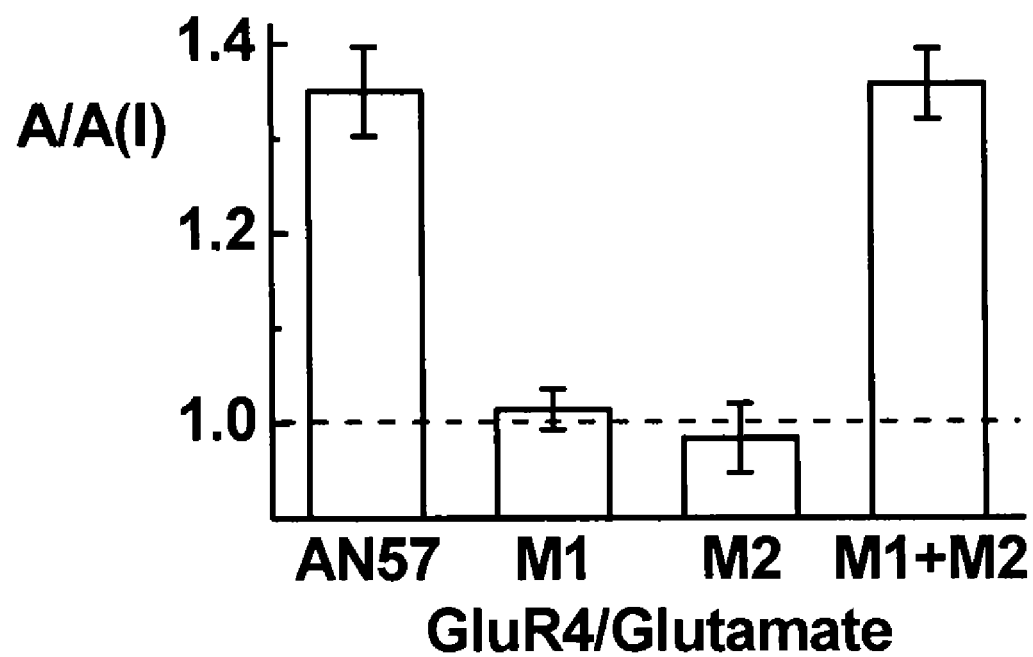
FIG. 8 shows that M1 and M2 individually do not inhibit the whole-cell response to glutamate via GluR2Q$_{flip}$ receptor channel. As with kainite, inhibition seen with unpurified AN57 is restored when the M1 and M2 are recombined.

To further test this hypothesis, we carried out a series of experiments (FIG. 4D). First, an equal molar mixture of the nonfunctional 53-nt transcript and the purified M2 yielded no inhibition, but the mixture of the 53-nt transcript and the purified M1 produced an inhibition as full as the mixture of purified M1 and M2 (FIG. 4D). This finding suggests that the 53-nt sequence apparently can form an M2-like structure, but not an M1-like structure. As a comparison, a nonfunctional, sequence-unrelated RNA, RN87, showed no inhibitory effect when mixed with either M1 or M2 (FIG. 4D). These results support the model (FIG. 4C) in which M1 and M2 bind to two separate sites, and further support the assumption that M1 and M2 are two structurally different species. Second, the results from the inhibition experiment using both agonist kainate (FIG. 7), instead of glutamate, and the GluR4$_{flip}$ AMPA receptor (FIG. 8), instead of GluR2Q$_{flip}$, showed that the binding of both M1 and M2 as a collaborating pair was required for inhibition. These results were consistent with the model (FIG. 4C) by which the inhibition by the aptamer would be expected even with a different agonist or with a different AMPA receptor. Knowing then that aptamer AN57 assumed two structures, M1 and M2, we further estimated the intrinsic inhibition constant or $K_I$ of M1 by using 10-fold excess of M2 or vice versa, according to Equ. 8. Under such a condition, $K_I$ for M1 and M2 was calculated to be 63±10 and 66±18 nM respectively, using Equation 9. These values suggest that both structures have nearly the same affinity for the GluR2Q$_{flip}$ receptor. Furthermore, the experiment using different ratios of M1 and M2 revealed that the stoichiometry of the inhibition is 1:1. It should be noted, however, that the aptamer could alternatively bind deep into the glutamate site to directly displace glutamate. Future structural investigations will be needed to identify sites of binding for both M1 and M2, and to distinguish these models accordingly. These investigations are now possible because both the X-ray and NMR structures for the extracellular binding domain of the GluR2Q$_{flip}$ receptor channel have been determined, and both the agonist-bound and the competitive antagonist-bound structures have been also resolved.

In one embodiment, the selection produces two structurally distinct RNA structures encoded by a single sequence. Both theoretical and experimental work has demonstrated the possibility that a single RNA sequence can assume multiple, distinctly folded structures. In the present instance, both structures are required to be present in a single preparation for a single function. Furthermore, these two structures assumed by the same sequence are stable, as monitored in native PAGE, even after extreme treatments such as boiling at 100° C. in the presence of 8 M urea, ethanol precipitation or freezing. Only after boiling at 100° C. in the presence of 50% formamide for 15 min did M1 partially unfold into something else but not into M2. Under the same condition, M2 remained essentially intact. The folding of these structures encoded by the same sequence is at the present unclear. Whether the sequence of AN57 assumes the structure of M1 or M2 is very likely determined by certain events during the transcription process. It is unlikely that these structures are converted by a thermodynamic equilibrium. The question of how these structures are formed is being pursued.

The stability of aptamer AN57 and its longer versions made it all possible for the aptamer to survive through multiple rounds of selections. For the same aptamer to be selected, the interaction between the aptamer and the receptor must have been strong as well. A previous study of the electrostatic field of the extracellular binding domain of the GluR2 AMPA receptor with glutamate, a negatively charged molecule at physiological pH, suggests that the surface of the receptor that makes up the entry of glutamate to its binding site is positively charged. Consequently this favorable electrostatic attraction is thought to steer glutamate to its site when a glutamate molecule approaches by free diffusion. As such, the negatively charged RNA molecules, like the one we selected, could bind to the positively charged receptor surface. Such a strong electrostatic attraction between the receptor and the stable RNA structures could be the basis of evolution through multiple rounds of selection, allowing the survival of such an aptamer from all other alternative, competing structures.

Figure 5:
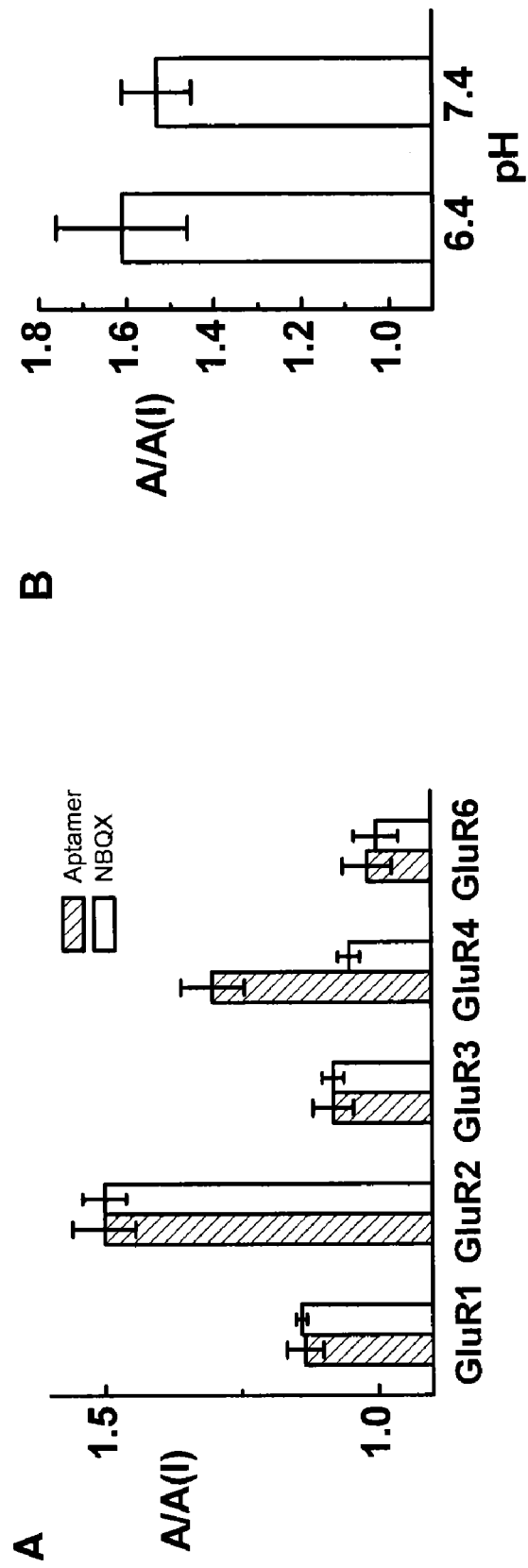
FIG. 5(A-B) shows that aptamer AN57 has inhibitory properties rivaling those of a known, very potent glutamate receptor inhibitor, NBQX.

The bi-structural feature of aptamer AN57 can be especially beneficial in developing more specific inhibitors/drugs against AMPA receptors than NBQX, the classical competitive inhibitor that displaces agonist from its binding site. This prediction is based on the novel mechanism of aptamer inhibition in that the competitive inhibition is realized in a simultaneous recognition of the receptor by two collaborating structures. Thus, using this collaborating pair should provide a greater specificity, than using a single molecule, like NBQX. Consistent with this prediction, AN57 was found to exhibit the improved specificity towards the GluR4$_{flip}$ channel, as compared to NBQX (FIG. 5A). Furthermore, AN57 showed no inhibition to the GluR6Q kainate receptor at the concentration tested (FIG. 5A). This property is desirable because kainate and AMPA receptor channels have different functionality in vivo. Therefore, as an initial proof of principle experiment, our results suggest the possibility of developing competitive inhibitors specific to some AMPA receptor subunits, perhaps by using another AMPA receptor subunit as the selection target.

Aptamer AN57 possesses additional superior inhibitory property over NBQX in that the aptamer retains the same inhibitory potency when the pH drops from 7.4 to 6.4 (FIG. 5B) whereas NBQX loses its potency by >3-fold. This acidic condition is clinically relevant to the infracted brain regions and thus the efficacy of inhibition by a potential drug at this acidic pH is a major requirement for an effective stroke treatment. Thus, aptamer AN57 is a promising template for potential drug development for the treatment of neurodegenerative conditions such as post-stroke cellular lesion.

The aptamer we have generated represents a unique, water-soluble template for future design of better inhibitors with potential therapeutic values in the diagnosis and the treatment of neurodegenerative disorders. The requirement of the simultaneous binding of the two structurally distinct aptamer species to an AMPA receptor to exert competitive inhibition in a collaborating fashion can be considered advantageous over the conventional displacement model by a single, competitive inhibitor. Such a use of this bi-structured aptamer may provide a higher regulatory ability as the lead compound in the design of subunit-specific inhibitors with nanomolar affinity for AMPA glutamate receptors.

Data Analysis

The inhibitory property of an RNA molecule was determined by the ratio of the glutamate-induced whole-cell current amplitude in the absence (A) and presence of the aptamer [A(I)]. A general scheme was formulated, below, in which binding of glutamate or ligand (L) to the unliganded receptor form (R) leads to the opening of the channel ($\overline{RL_2}$). Both steps of binding were assumed to have the same equilibrium dissociation constant ($K_1$). The number of ligand molecules bound to open an AMPA receptor channel is generally considered to be two.

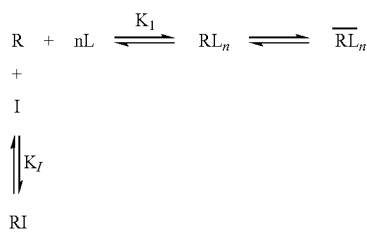

Shown in the same scheme is the competitive inhibition by an aptamer. By this mechanism, the apparent inhibition constant ($K_{I, app}$) can be obtained from the plot of A/A(I) versus the inhibitor concentration (I) using Equ. 8, and the intrinsic inhibition constant ($K_I$) can be calculated based on the $K_{I, app}$ and the glutamate concentration (L) using Equ. 9:

$$\frac{A}{A(I)} = 1 + \frac{I}{K_{I,app}} \quad \text{Equ. 8}$$

$$K_{I,app} = K_I \left[ \frac{1}{\Phi} \left( \frac{L}{K_1} \right)^2 + \left( \frac{L + K_1}{K_1} \right)^2 \right] \quad \text{Equ. 9}$$

where $\Phi^{-1}$ is the channel-opening equilibrium constant which we determined before. This scheme was used to estimate the apparent and intrinsic inhibition constants for aptamer AN57, assuming AN57 was a single molecule. The same equation was also used to estimate the intrinsic inhibition constant for M1 and M2 individually. In this case, the inhibition constant for one structure was determined when the other was 10-fold in excess in its molar concentration. Because binding of one structure did not elicit any current reduction, the single species-bound receptor state (i.e., either RM1 or RM2 state) was considered to be functionally equivalent to the R form (i.e., unliganded receptor form); only the RM1-M2 state was inhibitory.

Unless noted otherwise, each data point was an average of at least three measurements collected from at least three cells. Origin 7 (Origin Lab, Northampton, Mass.) was used for data analysis and plotting. Uncertainties reported refer to standard deviation from the mean.

The ultimate goal of identifying nucleic acid ligands such as those described herein is to develop selected aptamers as therapeutic and diagnostic agents for the treatment of ALS and other excitotoxic disorders.

Pharmaceutical Compositions

The invention, therefore, also includes pharmaceutical compositions containing nucleic acid aptamers of the invention. In some embodiments, the compositions are suitable for internal use and include an effective amount of a pharmacologically active compound of the invention, alone or in combination with one or more pharmaceutically acceptable carriers. The compounds are especially useful in that they have very good solubility.

Compositions of the invention can be used in a method for treating a patient or subject having a disease characterized by excessive activation of ionotropic glutamate receptors. Examples of diseases amenable to treatment in accordance with the present invention include amyotrophic lateral sclerosis (ALS), stroke, Alzheimer's disease and Parkinson's syndrome. The method involves administering to the patient or subject a composition comprising a nucleic acid aptamer that binds the receptor involved with the pathology, so that binding of the composition to the target alters the biological function of the target, thereby treating the pathology.

The patient or subject to be treated by the methods of this invention can be a mammal, or more particularly, a human.

In practice, the compounds or their pharmaceutically acceptable salts, are administered in amounts which will be sufficient to exert their desired biological activity, e.g., inhibiting the binding of glutamate to its receptor. The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

The magnitude of a prophylactic or therapeutic dose of aptamer in the acute or chronic management of disease will vary with the severity and nature of the condition to be treated and the route of administration. The dose and perhaps the dose frequency will also vary according to the age, body weight and response of the individual patient. It may be necessary to use dosages outside the usual ranges in some cases, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to treat conditions characterized by excessive activation of ionotropic glutamate receptors are encompassed by the above-described dosage amounts and dose frequency schedule.

Any suitable route of administration may be employed for providing the patient with an effective dosage of the aptamer of the invention. For example, oral, rectal, parenteral (subcutaneous, intramuscular, intravenous), transdermal, aerosol and like forms of administration may be employed. Dosage forms include tablets, troches, dispersions, suspensions, solutions, capsules, transdermal delivery systems, and the like.

The pharmaceutical compositions of the present invention comprise an aptamer of the invention as the active ingredient, and may also contain a pharmaceutically acceptable carrier, and optionally, other therapeutic ingredients.

REFERENCES

1. Cluskey, S., and Ramsden, D. B. (2001) Mechanisms of neurodegeneration in amyothrophic lateral sclerosis. *Mol Pathol* 54, 386-392.
2. Charles, T., and Swash, M. (2001) Amyotrophic lateral sclerosis: current understanding. *J Neurosci Nurs* 33, 245-253.
3. Silani, V., Braga, M., Cardin, V., and Scarlato, G. (2001) The pathogenesis of ALS: implications for treatment strategies. *Neurol Neurochir Pol* 35, 25-39.
4. Krampfl, K., Schlesinger, F., Wolfes, H., Dengler, R., and Bufler, J. (2001) Functional diversity of recombinant human AMPA type glutamate receptors: possible implications for selective vulnerability of motor neurons. *J Neurol Sci* 191, 19-23.
5. Iwasaki, Y., Ikeda, K., and Kinoshita, M. (1992) Plasma amino acid levels in patients with amyotrophic lateral sclerosis. *J Neurol Sci* 107, 219-222.
6. Shaw, P. J., Forrest, V., Ince, P. G., Richardson, J. P., and Wastell, H. J. (1995) CSF and plasma amino acid levels in motor neuron disease: elevation of CSF glutamate in a subset of patients. *Neurodegeneration* 4, 209-216.
7. Lin, C. L., Bristol, L. A., Jin, L., Dykes-Hoberg, M., Crawford, T., Clawson, L., and Rothstein, J. D. (1998) Aberrant RNA processing in a neurodegenerative disease: the cause for absent EAAT2, a glutamate transporter, in amyotrophic lateral sclerosis. *Neuron* 20, 589-602.
8. Saroff, D., Delfs, J. Kuznetsov, D., and Geula, C. (2000) Selective vulnerability of spinal cord motor neurons to non-NMDA toxicity. *Neuroreport* 11, 1117-1121.
9. Shaw, P. J., and Ince, P. G. (1997) Glutamate, excitotoxicity and amyotrophic lateral sclerosis. *J Neurol* 244, S3-14.
10. Urushitani, M., Nakamizo, T., Inoue, R., Sawada, H., Kihara, T., Honda, K., Akaike, A., and Shimohama, S. (2001) N-methyl-D-aspartate receptor-mediated mitochondrial Ca(2+) overload in acute excitotoxic motor neuron death: a mechanism distinct from chronic neurotoxicity after Ca(2+) influx. *J Neurosci Res* 63, 377-387.
11. Van Den Bosch, L., and Robberecht, W. (2000) Different receptors mediate motor neuron death induced by short and long exposures to excitotoxicity. *Brain Res Bull* 53, 383-388.
12. Nakamura, R., Kamakura, K., Hirata, A., and Kwak, S. (1997) Concentration-dependent changes in motor behavior produced by continuous intrathecal infusion of excitatory amino acids in the rat spinal cord. *Brain Res Protoc* 1, 385-390.
13. Rothstein, J. D., Jin, L., Dykes-Hoberg, M., and Kuncl, R. W. (1993) Chronic inhibition of glutamate uptake produces a model of slow neurotoxicity. *Proc Natl Acad Sci USA* 90, 6591-6595.
14. Brorson, J. R., Manzolillo, P. A., and Miller, R. J. (1994) Ca2+ entry via AMPA/KA receptors and excitotoxicity in cultured cerebellar Purkinje cells. *J Neurosci* 14, 187-197.
15. Turetsky, D. M., Canzoniero, L. M., Sensi, S. L., Weiss, J. H., Goldberg, M. P., and Choi, D. W. (1994) Cortical neurons exhibiting kainite-activated Co2+ uptake are selectively vulnerable to AMPA/kainite receptor-mediated toxicity. *Neurobiol Dis* 1, 101-110.
16. Jonas, P., and Spruston, N. (1994) Mechanisms shaping glutamate-mediated excitatory postsynaptic currents in the CNS. *Curr Opin Neurobiol* 4, 366-372.
17. Geiger, J. R., Melcher, T., Koh, D. S., Sakmann, B., Seeburg, P. H., Jonas, P., and Monyer, H. (1995) Relative abundance of subunit mRNAs determines gating and Ca2+ permeability of AMPA receptors in principal neurons and interneurons in rat CNS. *Neuron* 15, 193-204.
18. Williams, T. L., Ince, P. G., Oakley, A. E., and Shaw, P. J. (1996) An immunocytochemical study of the distribution of AMPA selective glutamate receptor subunits in the normal human motor system. *Neuroscience* 74.185-198.
19. Greig, A., Donevan, S. D., Mujtaba, T. J., Parks, T. N., and Rao, M. S. (2000) Characterization of the AMPA-activated receptors present on motoneurons. *J Neurochem* 74, 179-191.
20. Vandenberghe, W., Robberecht, W., and Brorson, J. R. (2000) AMPA receptor calcium permeability, GluR2 expression, and selective motoneuron vulnerability. *J Neurosci* 20, 123-132.
21. Dawson, D. A., Wadsworth, G., and Palmer, A. M. (2001) A comparative assessment of the efficacy and side-effect liability of neuroprotective compounds in experimental stroke. *Brain Res* 892, 344-350.
22. Madsen, U., Stensbol, T. B., and Krogsgaard-Larsen, P. (2001) Inhibitors of AMPA and kainite receptors. *Curr Med Chem* 8, 1291-1301.
23. Nikam, S. S., and Kornberg, B. E. (2001) AMPA receptor antagonists. *Curr Med Chem* 8, 155-170.
24. Honore, T., Davies, S. N., Drejer, J., Fletcher, E. J., Jacobsen, P., Lodge, D., and Nielsen, F. E. (1998) Quinoxalinediones: potent competitive non-NMDA glutamate receptor antagonists. *Science* 241, 701-703.
25. Sheardown, M. J., Nielsen, E. O., Hansen, A. J., Jacobsen, P., and Honore, T. (1990) 2,3-Dihydroxy-6-nitro-7-sulfamoyl-benzo(F)quinoxaline: a neuroprotectant for cerebral ischemia. *Science* 247, 571-574.
26. Abraham, G., Solyom, S., Csuzdi, E., Berzsenyi, P., Ling, I., Tarnawa, I., Hamori, T., Pallagi, I., Horvath, K., Andrasi, F., Kapus, G., Harsing, L. G., Jr., Kiraly, I., Patthy, M., and Horvath, G. (2000) New non competitive AMPA antagonists. *Bioorg Med Chem* 8, 2127-2143.
27. Jackson, H., and Usherwood, P. N. (1988) Spider toxins as tools for dissecting elements of excitatory amino acid transmission. *Trends Neurosci* 11, 278-283.
28. Iino, M., Koike, M., Isa, T., and Ozawa, S. (1996) Voltage-dependent blockage of Ca(2+)-permeable AMPA receptors by joro spider toxin in cultured rat hippocampal neurons. *J Physiol (Lond)* 496, 431-437.
29. Brackley, P., Goodnow, R., Jr., Nakanishi, K., Sudan, H. L., and Usherwood, P. N. (1990) Spermine and philantho- 29. toxin potentiate excitatory amino acid responses of Xenopus oocytes injected with rat and chick brain RNA. *Neurosci Lett* 114, 51-56.
30. Dingledine, R., Borges, K., Bowie, D., and Traynelis, S. F. (1999) The glutamate receptor ion channels. *Pharmacol Rev* 51, 7-61.
31. Hollmann, M., and Heinemann, S. (1994) Cloned glutamate receptors. *Annu Rev Neurosci* 17, 31-108.
32. Hollmann, M., Hartley, M., and Heinemann, S. (1991) Ca2+ permeability of KA-AMPA-gated glutamate receptor channels depends on subunit composition. *Science* 252, 851-853.
33. Seeburg, P. H. (1993) The TINS/TiPS Lecture, The molecular biology of mammalian glutamate receptor channels. *Trends neurosci* 16, 359-365.
34. Nakanishi, N., Shneider, N. A., and Axel, R. (1990) A family of glutamate receptor genes: evidence for the formation of heteromultimeric receptors with distinct channel properties. *Neuron* 5, 569-581.
35. Collingridge, G. L., and Lester, R. A. (1989) Excitatory amino acid receptors in the vertebrate central nervous system. *Pharmacol Rev* 41, 143-210.
36. Wo, Z. G., and Oswald, R. E. (1995) Unraveling the modular design of glutamate-gated ion channels. *Trends Neurosci* 18, 161-168.
37. Hollmann, M., Maron, C., and Heinemann, S. (1994) N-glycosylation site tagging suggests a three transmembrane domain topology for the glutamate receptor GluR1. *Neuron* 13, 1331-1343.
38. Bennett, J. A., and Dingledine, R. (1995) Topology profile for a glutamate receptor: three transmembrane domains and a channel-lining reentrant membrane loop. *Neuron* 14, 373-384.
39. Armstrong, N., Sun, Y., Chen, G. Q., and Gouaux, E. (1998) Structure of a glutamate-receptor ligand-binding core in complex with kainite. *nature* 395, 913-917.
40. Dev, K. K., and Henley, J. M. (1998) The regulation of AMPA receptor-binding sites. *Mol Neurobiol* 17, 33-58.
41. Trist, D. G. (2000) Excitatory amino acid agonists and antagonists: pharmacology and therapeutic applications. *Pharm Acta Helv* 74, 221-229.
42. Turski, L., Huth, A., Sheardown, M., McDonald, F., Neuhaus, R., Schneider, H. H., Dirnagl, U., Wiegand, F., Jacobsen, P., and Ottow, E. (1998) ZK200775: a phosphonate quinoxalinedione AMPA antagonist for neuroprotection in stroke and trauma. *Proc Natl Acad Sci U S A* 95, 10960-10965.
43. Swanson, G. T., Kamboj, S. K., and Cull-Candy, S. G. (1997) Single-channel properties of recombinant AMPA receptors depend on RNA editing, splice variation, and subunit composition. *J Neurosci* 17, 58-69.
44. White, R. R., Sullenger, B. A., and Rusconi, C. P. (2000) Developing aptamers into therapeutics [In Process Citation]. *J Clin Invest* 106, 929-934.
45. Brody, E. N., and Gold, L. (2000) Aptamers as therapeutic and diagnostic agents [In Process Citation]. *J Biotechnol* 74, 5-13.
46. Hesselberth, J., Robertson, M. P., Jhaveri, S., and Ellington, A. D. (2000) In vitro selection of nucleic acids for diagnostic applications [In Process Citation]. *J Biotechnol* 74, 15-25.
47. Brody, E. N., Willis, M. C., Smith, J. D., Jayasena, S., Zichi, D., and Gold, L. (1999) The use of aptamers in large arrays for molecular diagnostics. *Mol Diagn* 4, 381-388.
48. Ellington, A. D., and Szostak, J. W. (1990) In vitro selection of RNA molecules that bind specific ligands. *Nature* 346, 818-822.
49. Tuerk, C., and Gold, L. (1990) Systematic evolution of ligands by exponential enrichment: RNA ligands to bacteriophage T4 DNA polymerase. *Science* 249, 505-510.
50. Jhaveri, S., Rajendran, M., and Ellington, A. D. (2000) In vitro selection of signaling aptamers. *Nat Biotechnol* 18, 1293-1297.
51. Stojanovic, M. N., de Prada, P., and Landry, D. W. (2001) Aptamer-based folding fluorescent sensor for cocaine. *J Am Chem Soc* 123, 4928-4931.
52. Ruckman, J., Green, L. S., Beeson, J., Waugh, S., Gillette, W. L., Henninger, D. D., Claesson-Welsh, L., and Janjic, N. (1998) 2'-Fluoropyrimidine RNA-based aptamers to the 165-amino acid form of vascular endothelial growth factor (VEGF165). Inhibition of receptor binding and VEGF-induced vascular permeability through interactions requiring the exon 7-encoded domain. *J Biol Chem* 273, 20556-20567.
53. Sun, S. (2000) Technology evaluation: SELEX, Gilead Sciences Inc. *Curr Opin Mol Ther* 2, 100-105.
54. Hess, G. P., and Grewer, C. (1998) Development and application of caged ligands for neurotransmitter receptors in transient kinetic and neuronal circuit mapping studies. *Methods Enzymol* 291, 443-473.
55. Niu, L., and Hess, G. P. (1993) An acetylcholine receptor regulatory site in BC3H1 cells: characterized by laser-pulse photolysis in the microsecond-to-millisecond time region. *Biochemistry* 32, 3831-3835.
56. Niu, L., Abood, L. G., and Hess, G. P. (1995) Cocaine: mechanism of inhibition of a muscle acetylcholine receptor studied by a laser-pulse photolysis technique. *Proc Natl Acad Sci U S A* 92, 12008-12012.
57. Hess, G. P. (1993) Determination of the chemical mechanism of neurotransmitter receptor-mediated reactions by rapid chemical kinetic techniques. *Biochemistry* 32, 989-1000.
58. Kaplan, J. H. (1990) Photochemical manipulation of divalent cation levels. *Annu Rev Physiol* 52, 897-914.
59. McCray, J. A., and Trentham, D. R. (1989) Properties and uses of photoreactive caged compounds. *Annu Rev Biophys Chem* 18, 239-270.
60. Matsubara, N., Billington, A. P., and Hess, G. P. (1992) How fast does an acetylcholine receptor channel open? Laser-pulse photolysis of an inactive precursor of carbamoylcholine in the microsecond time region with BC3H1 cells. *Biochemistry* 31, 5507-5514.
61. Wieboldt, R., Gee, K. R., Niu, L., Ramesh, D., Carpenter, B. K., and Hess, G. P. (1994) Photolabile precursors of glutamate: synthesis, photochemical properties, and activation of glutamate receptors on a microsecond time scale. *Proc Natl Acad Sci U S A* 91, 8752-8756.
62. Gee, K. R., Niu, L., Schaper, K., Jayaraman, V., and Hess, G. P. (1999) Synthesis and photochemistry of a photolabile precursor of N-methyl-D-aspartate (NMDA) that is photolyzed in the microsecond time region and is suitable for chemical kinetic investigations of the NMDA receptor. *Biochemistry* 38, 3140-3147.
63. Niu, L., Gee, K. R., Schaper, K., and Hess, G. P. (1996) Synthesis and photochemical properties of a kainate precursor and activation of kainate and AMPA receptor channels on a microsecond time scale. *Biochemistry* 35, 2030-2036.
64. Hess, G. P. Ulrich, H., Breitinger, H. G., Niu, L., Gameiro, A. M., Grewer, C., Srivastava, S., Ippolito, J. E., Lee, S. M., Jayaraman, V., and Coombs, S. E. (2000) Mechanism-based discovery of ligands that counteract inhibition of the nicotinic acetylcholine receptor by cocaine and MK-801. *Proc Natl Acad Sci U S A* 97, 13895-13900.

65. Ulrich, H., Ippolito, J. E., Pagan, O. R., Eterovic, V. A., Hann, R. M., Shi, H., L is, J. T., Eldefrawi, M. E., and Hess, G. P. (1998) In vitro selection of RNA molecules that displace cocaine from the membrane-bound nicotinic acetylcholine receptor. *Proc Natl Acad Sci U S A* 95, 14051-14056.

66. Bruel, C., Cha, K., Niu, L., Reeves, P. J., and Khorana, H. G. (2000) Rhodopsin kinase: two mAbs binding near the carboxyl terminus cause time-dependent inactivation. *Proc Natl Acad Sci U S A* 97, 3010-3015.

67. Shi, H., Hoffman, B. E., and L is, T. J. (1997) A specific RNA hairpin loop structure binds the RNA recognition motifs of the Drosophila SR protein B52. *Mol Cell Biol* 17, 2649-2657.

68. Camu, W., and Henderson, C. E. (1992) Purification of embryonic rat motoneurons by panning on a monoclonal antibody to the low-affinity NGF receptor. *J Neurosci Methods* 44, 59-70.

69. Camu, W., and Henderson, C. E. (1994) Rapid purification of embryonic rat motoneurons: an in vitro model for studying MND/ALS pathogenesis. *J Neurol Sci* 124, 73-74.

70. Washburn, M. S., and Dingledine, R. (1996) Block of alpha-amino-3-hydroxy-5-methyl-4-isoxazolepropionic acid (AMPA) receptors by polyamines and polyamine toxins. *J Pharmacol Exp Ther* 278, 669-678.

71. Gold, L. (1995) Oligonucleotides as research, diagnostic, and therapeutic agents. *J Biol Chem* 270, 13581-13584.

72. Chen, C., and Okayama, H. (1987) High-efficiency transformation of mammalian cells by plasmid DNA. *Mol Cell Biol* 7, 2745-2752.

73. Hamill, O. P., Marty, A., Neher, E., Sakmann, B., and Sigworth, F. J. (1981) Improved patch-clamp techniques for high-resolution current recording from cells and cell-free membrane patches. *Pflugers Arch* 391, 85-100.

74. Udgaonkar, J. B., and Hess, G. P. (1987) Chemical kinetic measurements of a mammalian acetylcholine receptor by a fast-reaction technique. *Proc Natl Acad Sci U S A* 84, 8758-8762.

75. L. I. Bruijn, T. M. Miller, D. W. Cleveland, *Annu Rev Neurosci* 27, 723 (2004).

76. S. Solyom, I. Tarnawa, *Curr Pharm Des* 8, 913 (2002).

77. K. Umemura et al., *J Clin Pharmacol* 37, 719 (1997).

78. G. Li, W. Pei, L. Niu, *Biochemistry* 42, 12358 (2003).

79. G. Li, Z. Sheng, Z. Huang, L. Niu, *Biochemistry* 44, 5835 (2005).

80. L. Nowak, P. Bregestovski, P. Ascher, A. Herbet, A. Prochiantz, *Nature* 307, 462 (1984).

81. P. R. Heath, P. J. Shaw, *Muscle Nerve* 26, 438 (2002).

82. P. Van Damme, M. Leyssen, G. Callewaert, W. Robberecht, L. Van Den Bosch, *Neurosci Lett* 343, 81 (2003).

83. T. Weiser, *Curr Drug Targets CNS Neurol Disord* 4, 153 (2005).

84. M. Shimizu-Sasamata et al., *J Pharmacol Exp Ther* 276, 84 (1996).

85. X. Fan, H. Shi, K. Adelman, J. T. L is, *Proc Natl Acad Sci U S A* 101, 6934 (2004).

86. H. Shi, B. E. Hoffman, J. T. Lis, *Proc Natl Acad Sci U S A* 96, 10033 (1999).

87. R. R. Breaker, *Nature* 432, 838 (2004).

88. M. Zuker, *Nucleic Acids Res* 31, 3406 (2003).

89. G. Li, R. E. Oswald, L. Niu, *Biochemistry* 42, 12367 (2003).

90. R. Knight, M. Yarus, *Nucleic Acids Res* 31, e30. (2003).

91. N. Armstrong, E. Gouaux, *Neuron* 28, 165 (2000).

92. R. L. McFeeters, R. E. Oswald, *Biochemistry* 41, 10472 (2002).

93. M. A. Huynen, P. F. Stadler, W. Fontana, *Proc Natl Acad Sci U S A* 93, 397 (1996).

94. E. A. Schultes, D. P. Bartel, *Science* 289, 448 (2000).

95. M. Kubo, E. Ito, *Proteins* 56, 411 (2004).

J. Lerma, A. V. Paternain, A. Rodriguez-Moreno, J. C. Lopez-Garcia, *Physiol Rev* 81, 971 (2001).

97. G. Li, W. Pei, L. Niu, *Biochemistry* 42, 12358 (2003).

98. C. Chen, H. Okayama, *Mol Cell Biol* 7, 2745 (1987).

99. Z. Huang, G. Li, W. Pei, L. A. Sosa, L. Niu, *J Neurosci Methods* 142, 159 (2005).

100. O. P. Hamill, A. Marty, E. Neher, B. Sakmann, F. J. Sigworth, *Pflugers Arch* 391, 85 (1981).

101. J. B. Udgaonkar, G. P. Hess, *Proc Natl Acad Sci U S A* 84, 8758 (1987).

---

The invention claimed is:

1. An isolated nucleic acid that binds to an α-amino-3-hydroxy-5-methyl-4-isoxazole proionate (AMPA) subtype glutamate receptor, wherein said nucleic acid is an RNA and comprises a nucleotide sequence selected from the group consisting of SEQ ID NO.: 1, SEQ ID NO.: 2, SEQ ID NO.: 3, SEQ ID NO.: 4, SEQ ID NO.: 5, SEQ ID NO.: 7, SEQ ID NO.: 8, SEQ ID NO.: 9, SEQ ID NO.: 10 and SEQ ID NO.: 11.

2. The isolated nucleic acid of claim 1, wherein the nucleic acid contains between 25 and 150 nucleotides.

3. The isolated nucleic acid of claim 1, wherein the nucleic acid contains between 50 and 100 nucleotides.

4. The isolated nucleic acid of claim 1, wherein said nucleic acid contains one or more chemically modified nucleotides.

5. The isolated nucleic acid of claim 1 wherein the one or more chemically modified nucleotides has a 2' fluoro substituent.

6. The isolated nucleic acid of claim 1 wherein the nucleic acid can have one or more secondary structures.

7. The isolated nucleic acid of claim 1, wherein said nucleic acid inhibits glutamate receptor function.

8. The isolated nucleic acid of claim 1, wherein said nucleic acid has a $K_I$ in the range of 100 to 200 nM.

9. A preparation of the isolated nucleic acids of claim 1 having a single nucleotide sequence, wherein the preparation comprises nucleic acids having more than one secondary structures.

10. The preparation of claim 9, wherein said isolated nucleic acids contained in said preparation have two secondary structures, both of which are required for inhibition.

11. An isolated DNA that codes for an RNA wherein the RNA comprises a nucleotide sequence selected from the group of SEQ ID NOS.: 1 to 11.

12. A method of inhibiting an AMPA subtype glutamate receptor comprising contacting said receptor with the nucleic acid of claim 1.

13. A composition comprising a nucleic acid according to claim 1 and a pharmaceutically acceptable carrier.

* * * * *

SEQUENCE LISTING

```
<160> NUMBER OF SEQ ID NOS: 11

<210> SEQ ID NO 1
<211> LENGTH: 82
<212> TYPE: RNA
<213> ORGANISM: Artificial
<220> FEATURE:
<221> NAME/KEY: misc_feature
<222> LOCATION: (1)..(82)
<223> OTHER INFORMATION: aptamer that binds to glutamate receptor, AMPA
      subtype

<400> SEQUENCE: 1
gggcgaauuc acugccaucu aggcaguaac caggaguuag uaggacaagu uucguaacca    60
guuaagaugg uaaaguacua ca                                             82

<210> SEQ ID NO 2
<211> LENGTH: 83
<212> TYPE: RNA
<213> ORGANISM: Artificial
<220> FEATURE:
<221> NAME/KEY: misc_feature
```

```
<223> OTHER INFORMATION: aptamer that binds to glutamate receptor, AMPA
      subtype

<400> SEQUENCE: 2
gggcgaauuc acugccaucu aggcuugagu uggaugccug cgcuuaacug cgcggcuuau    60
ccagagguau acguaguacu aca                                            83

<210> SEQ ID NO 3
<211> LENGTH: 83
<212> TYPE: RNA
<213> ORGANISM: Artificial
<220> FEATURE:
<221> NAME/KEY: misc_feature
<223> OTHER INFORMATION: aptamer that binds to glutamate receptor, AMPA
      subtype

<400> SEQUENCE: 3
gggcgaauuc acugccaucu aggcgcuugu uggaccaaga gacacccacg aauggucguc    60
ucacgucaca auugaguacu aca                                            83

<210> SEQ ID NO 4
<211> LENGTH: 83
<212> TYPE: RNA
<213> ORGANISM: Artificial
<220> FEATURE:
<221> NAME/KEY: misc_feature
<222> LOCATION: (1)..(83)
<223> OTHER INFORMATION: aptamer that binds to glutamate receptor, AMPA
      subtype

<400> SEQUENCE: 4
gggcgaauuc acugccaucu aggccgucuu cgugacaaag guggaacuug augguuagac    60
gaaaaaaccc cagaaguacu aca                                            83

<210> SEQ ID NO 5
<211> LENGTH: 98
<212> TYPE: RNA
<213> ORGANISM: Artificial
<220> FEATURE:
<221> NAME/KEY: misc_feature
<222> LOCATION: (1)..(98)
<223> OTHER INFORMATION: aptamer that binds to glutamate receptor, AMPA
      subtype

<400> SEQUENCE: 5
gggcgaauuc acugccaucu aggcaguaac caggaguuag uaggacaagu uucguaacca    60
guuaagaugg uaaaguacua caagcuucug gacucggu                            98

<210> SEQ ID NO 6
<211> LENGTH: 57
<212> TYPE: RNA
<213> ORGANISM: Artificial
<220> FEATURE:
<221> NAME/KEY: misc_feature
<222> LOCATION: (1)..(57)
<223> OTHER INFORMATION: aptamer that binds to glutamate receptor, AMPA
      subtype

<400> SEQUENCE: 6
gggcgaauuc acugccaucu aggcaguaac caggaguuag uaggacaagu uucgucc       57

<210> SEQ ID NO 7
<211> LENGTH: 98
<212> TYPE: RNA
<213> ORGANISM: Artificial
<220> FEATURE:
```

```
<221> NAME/KEY: misc_feature
<222> LOCATION: (1)..(98)
<223> OTHER INFORMATION: aptamer that binds to glutamate receptor, AMPA
      subtype

<400> SEQUENCE: 7
gggcgaauuc acugccaucu aggcaguaac caggaguuag uaggacaagu uucguaacca    60
guuaagaugg uaaaguacua caagcuucug gacucggu                           98

<210> SEQ ID NO 8
<211> LENGTH: 86
<212> TYPE: RNA
<213> ORGANISM: Artificial
<220> FEATURE:
<221> NAME/KEY: misc_feature
<222> LOCATION: (1)..(86)
<223> OTHER INFORMATION: aptamer that binds to glutamate receptor, AMPA
      subtype

<400> SEQUENCE: 8
gggcgaauuc acugccaucu aggcaguaac caggaguuag uaggacaagu uucguaacca    60
guuaagaugg uaaaguacua caagcu                                        86

<210> SEQ ID NO 9
<211> LENGTH: 87
<212> TYPE: RNA
<213> ORGANISM: Artificial
<220> FEATURE:
<221> NAME/KEY: misc_feature
<222> LOCATION: (1)..(87)
<223> OTHER INFORMATION: aptamer that binds to glutamate receptor, AMPA
      subtype

<400> SEQUENCE: 9
gggcgaauuc acugccaucu aggcuugagu uggaugccug cgcuuaacug cgcggcuuau    60
ccagagguau acguaguacu acaagcu                                       87

<210> SEQ ID NO 10
<211> LENGTH: 87
<212> TYPE: RNA
<213> ORGANISM: Artificial
<220> FEATURE:
<221> NAME/KEY: misc_feature
<222> LOCATION: (1)..(87)
<223> OTHER INFORMATION: aptamer that binds to glutamate receptor, AMPA
      subtype

<400> SEQUENCE: 10
gggcgaauuc acugccaucu aggccgucuu cgugacaaag guggaacuug augguuagac    60 gaaaaaccc cagaaguacu acaagcu                                        87

<210> SEQ ID NO 11
<211> LENGTH: 87
<212> TYPE: RNA
<213> ORGANISM: Artificial
<220> FEATURE:
<221> NAME/KEY: misc_feature
<222> LOCATION: (1)..(87)
<223> OTHER INFORMATION: aptamer that binds to glutamate receptor, AMPA
      subtype

<400> SEQUENCE: 11
gggcgaauuc acugccaucu aggcgcuugu uggaccaaga gacacccacg aauggucguc    60
ucacgucaca auugaguacu acaagcu                                       87
```